United States Patent
Jung et al.

(10) Patent No.: US 8,403,664 B2
(45) Date of Patent: Mar. 26, 2013

(54) DENTAL OBTURATION SYSTEM

(75) Inventors: Du-Rok Jung, Goyang-Si (KR); Kyoung-Soo Shin, Goyang-si (KR)

(73) Assignee: DXM Co., Ltd., Goyang, Gyeonggi-Do (KR)

( * ) Notice: Subject to any disclaimer, the term of this patent is extended or adjusted under 35 U.S.C. 154(b) by 38 days.

(21) Appl. No.: 13/003,242

(22) PCT Filed: Jul. 6, 2009

(86) PCT No.: PCT/KR2009/003683
§ 371 (c)(1),
(2), (4) Date: Jan. 7, 2011

(87) PCT Pub. No.: WO2010/005216
PCT Pub. Date: Jan. 14, 2010

(65) Prior Publication Data
US 2011/0165537 A1     Jul. 7, 2011

(30) Foreign Application Priority Data

Jul. 8, 2008   (KR) .................. 20-2008-0009066 U

(51) Int. Cl.
*A61C 3/00*     (2006.01)
*A61C 5/02*     (2006.01)
*A61F 7/12*     (2006.01)
*F27B 14/06*    (2006.01)

(52) U.S. Cl. ............ 433/32; 433/81; 604/113; 219/424; 219/426

(58) Field of Classification Search .................... 433/25, 433/28–29, 32, 36, 44, 50, 52, 75, 80–83, 433/89–90, 98–99, 114–115, 121–122, 141, 433/146–147, 152–154, 215, 224; 439/11, 439/13–19, 21, 372; 222/144, 146.2, 146.5, 222/386–391, 566–574; 604/60, 61, 82, 604/113, 114, 181, 185, 187, 214, 218, 228, 604/232, 233; 219/146.5, 421, 424, 426, 219/541; 401/1, 2
See application file for complete search history.

(56) References Cited

U.S. PATENT DOCUMENTS

| 3,286,076 | A | * | 11/1966 | Finch ............................ 219/230 |
| 3,434,477 | A | * | 3/1969 | Thomas, Jr. ................... 606/25 |
| 3,973,697 | A | * | 8/1976 | Crum et al. ..................... 222/47 |
| 2002/0127512 | A1 | * | 9/2002 | Chen et al. .................... 433/119 |

FOREIGN PATENT DOCUMENTS

WO    WO 2006083114 A1 *    8/2006

* cited by examiner

*Primary Examiner* — Cris L Rodriguez
*Assistant Examiner* — Justin O'Donnell
(74) *Attorney, Agent, or Firm* — Edwards Wildman Palmer LLP

(57) ABSTRACT

A dental obturation system, which is configured such that a power terminal unit is installed between a rotary unit and a cartridge unit such that a heating unit can heat a filling material and a needle member, mounted to the front end of a main body having a battery therein, can be rotated while applying the heated filling material to a root canal, so that an operator can easily and conveniently administer dental treatment without changing his/her posture or the orientation of the main body according to the location of a decayed tooth of a patient.

9 Claims, 9 Drawing Sheets

DENTAL OBTURATION SYSTEM

CROSS-REFERENCES TO RELATED APPLICATIONS

This application is a U.S. national phase application, pursuant to 35 U.S.C. §371, of PCT/KR2009/003683, filed Jul. 6, 2009, designating the United States, which claims priority to Korean Application No. 20-2008-0009066, filed Jul. 8,2008. The entire contents of the aforementioned patent applications are incorporated herein by this reference.

BACKGROUND OF THE INVENTION

1. Field of the Invention

The present invention relates, in general, to dental obturation systems and, more particularly, to a dental obturation system, which can heat and melt gutta-percha (root canal filling rubber) and can obturate a root canal with the gutta-percha under high pressure using a micro tube while the nerves of a patient receive dental treatment.

2. Description of the Related Art

Generally, methods of treating a decayed tooth for a patient in a dental clinic have been executed by removing a decayed part from the tooth using dental files and by filling a root canal with a filling material (root canal filling cement or a sealer), and thereby sealing the root canal prior to applying a dental prosthesis to the tooth. Particularly when an endodontium has been injured or infected in the above state, the injured or infected endodontium must be removed prior to filling the root canal with the filling material. The process of filling the root canal with the filling material uses a gutta-percha cone, which is a temporary filling material capable of aiding the main filling material such that the main filling material can efficiently fill the root canal and can completely seal the root canal. The gutta-percha is natural vegetable extract, which naturally is in a semisolid state at room temperature, but is provided in the form of solidified rubber by pressurizing or heating the semisolid gutta-percha. The gutta-percha in the form of the solidified rubber has been generally called "white gutta-percha".

The white gutta-percha is mixed with zinc oxide, barium sulfate, wax, pigment, etc. using a roll or a mixer and is extruded in the form of a plate, and is cut into gutta-percha cones of various sizes. Gutta-percha cones are materials which are widely and preferably used in root canal treatment in recent years and are known as a material which is compatible with a living body because it is not poisonous to a root apex. The marketed gutta-percha cones include standardized cones and accessory cones, in which the standardized cones have the same shape as that of dental files.

In administering dental treatment to a patient in need of nerve repair, the infected part of an endodontium is cut and infected nervous tissue is removed using dental files, and, in order to prevent a new source of infection from forming in a root canal, a filling material is applied to a root canal wall and a gutta-percha cone having a size appropriate to the size of the root canal is inserted into the root canal, thus allowing the filling material to be fixed both to a main root canal and to a sub-root canal. In the above state, it is important to bring the gutta-percha cone into complete contact both with the root canal wall and with the root apex.

When the root canal has been obturated as described above, the filling state of the filling material in the root canal is examined by X-rays and, thereafter, the gutta-percha cone is removed from the root canal. To remove the gutta-percha cone from the root canal, a heated excavator, a heated endodontic plugger or a heated spreader have been used.

A dental obturation system, which has been used to apply the gutta-percha cone to the root canal such that the gutta-percha cone can be brought into complete contact with the root canal wall during the dental treatment, typically includes a main body, a hand grip part, a power unit for supplying electricity to the system, a heating unit, and a needle member (micro tube) mounted to a front end of the main body.

However, the conventional dental obturation system is problematic in that both the heating unit and the micro tube are fixed to the main body, so that it is not easy to manipulate the system.

Described in detail, when the dental obturation system is used in a dental clinic, the micro tube is typically used after bending it so as to realize easy application of the filling material into a tooth. However, the bending direction and the bending angle of the micro tube must be different to suit the affected part of a patient, which may be situated in an anterior tooth, a posterior tooth, a maxillary tooth or a mandibular tooth. Therefore, when an operator cannot freely move his/her hands or cannot freely manipulate the dental obturation system while using the system, the operator may not easily use the system. Particularly, the gutta-percha must be heated at a high temperature exceeding 200° C., so that the patient and the operator are exposed to a burn when the dental treatment is being administered.

SUMMARY OF THE INVENTION

Accordingly, the present invention has been made keeping in mind the above problems occurring in the related art, and the present invention is intended to propose a dental obturation system, in which a rotatable heating unit is provided, and thereby, the direction of a needle member (a micro tube) connected to the heating unit can be easily controlled.

In order to achieve the above object, according to one aspect of the present invention, there is provided a dental obturation system, comprising: a main body including a grip housing receiving a battery therein and an upper housing mounted to an upper end of the grip housing; a needle member mounted to a front end of the upper housing and filling a place requiring a dental treatment with a heated filling material; a heating unit connected to the needle member and heating the filling material to be fed to the needle member; a rotary unit installed in the upper housing in a state in which the rotary unit is combined with the heating unit and can rotate along with the heating unit; a cartridge unit for receiving therein the filling material supplied from an outside, the cartridge unit being securely installed in the upper housing such that the cartridge unit faces the rotary unit; a piston unit movably installed in the upper housing and feeding the filling material from the cartridge unit under pressure in a direction toward both the heating unit and the needle member; a trigger rotatably mounted to the main body and actuating the piston unit, thus feeding the filling material; and a power terminal unit installed both in the rotary unit and in the cartridge unit and maintaining an electric connection between the rotary unit and the cartridge unit such that the power terminal unit can apply electricity of the battery to the heating unit even when the rotary unit is rotating.

In the dental obturation system, the rotary unit may comprise: a bore for allowing the piston unit to be moved therethrough; an annular groove formed around an outer circumferential surface of the rotary unit; and a bushing part protruding from an end of the rotary unit facing the cartridge unit and holding the power terminal unit, with a guide rib provided in the upper housing for engaging with the annular groove and thereby guiding a rotation of the rotary unit while preventing forward or backward movement of the rotary unit.

Further, the cartridge unit, which is securely installed in the upper housing such that it faces the rotary unit, may comprise: a bore for allowing the piston unit to be moved therethrough; an inlet opening formed in an outer circumferential wall of the cartridge unit so as to allow the filling material to be fed into the bore of the cartridge unit; and a pair of terminal support holes for supporting the power terminal unit.

Further, the power terminal unit may comprise: a first terminal member securely mounted to the rotary unit and electrically connected to the heating unit; and a pair of second terminal members installed in the respective terminal support holes of the cartridge unit and maintaining a state in which the second terminal members are electrically connected to the first terminal member.

Further, the first terminal member may comprise: an annular substrate fitted over the bushing part of the rotary unit through an opening and having a locking notch, which is formed in an edge of the opening and is engaged with a locking rib formed around an outer circumferential surface of the bushing part; and first and second annular terminals concentrically protruding from a surface of the substrate and having different radii, wherein the pair of second terminal members may come into contact with the first and second terminals, respectively.

Further, each of the first and second terminals may protrude from the surface of the substrate such that each of the first and second terminals has a semi-circular cross-section.

Further, the upper housing may be provided with a charging port for charging the cartridge unit with the filling material, wherein the dental obturation system may further comprise a covering member movably installed in a space between the upper housing and the cartridge unit such that the covering member can open or close the charging port.

Further, the piston unit may comprise: a piston member installed in the upper housing such that the piston member can be moved through the cartridge unit, the rotary unit and the heating unit; a piston support installed in the upper housing and guiding movement of the piston member; and an anti-reverse rod combined with the piston member and securely mounted to the upper housing such that the anti-reverse rod can restrict reverse movement of the piston member.

Further, the dental obturation system may further comprise: a protective cover made of a silicone material and installed around the heating unit so as to cover the heating unit.

Further, the dental obturation system may further comprise: a Teflon pipe installed between the heating unit and the protective cover and intercepting radiant heat emitted from the heating unit.

As described above, the dental obturation system according to the present invention is provided with the power terminal unit, which can continuously apply electricity of the battery to the heating unit in a state in which the heating unit and the rotary unit are rotated along with each other, so that an operator can easily and conveniently administer dental treatment while rotating the needle member connected to the heating unit.

Therefore, the dental obturation system of the present invention is advantageous in that the operator can easily and conveniently administer dental treatment without changing his/her posture or the orientation of the dental obturation system according to the location of a decayed tooth of a patient.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
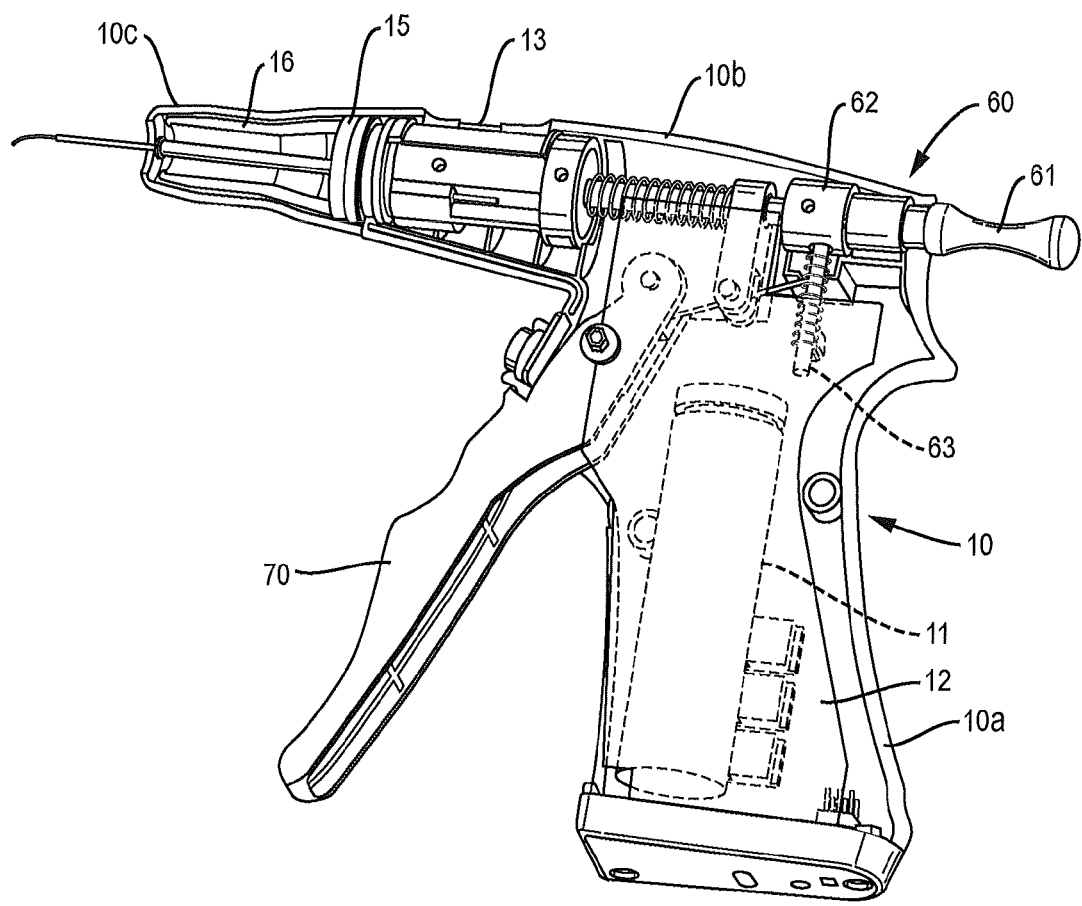
FIG. 1 is a perspective view illustrating a dental obturation system according to an embodiment of the present invention.
Figure 2:
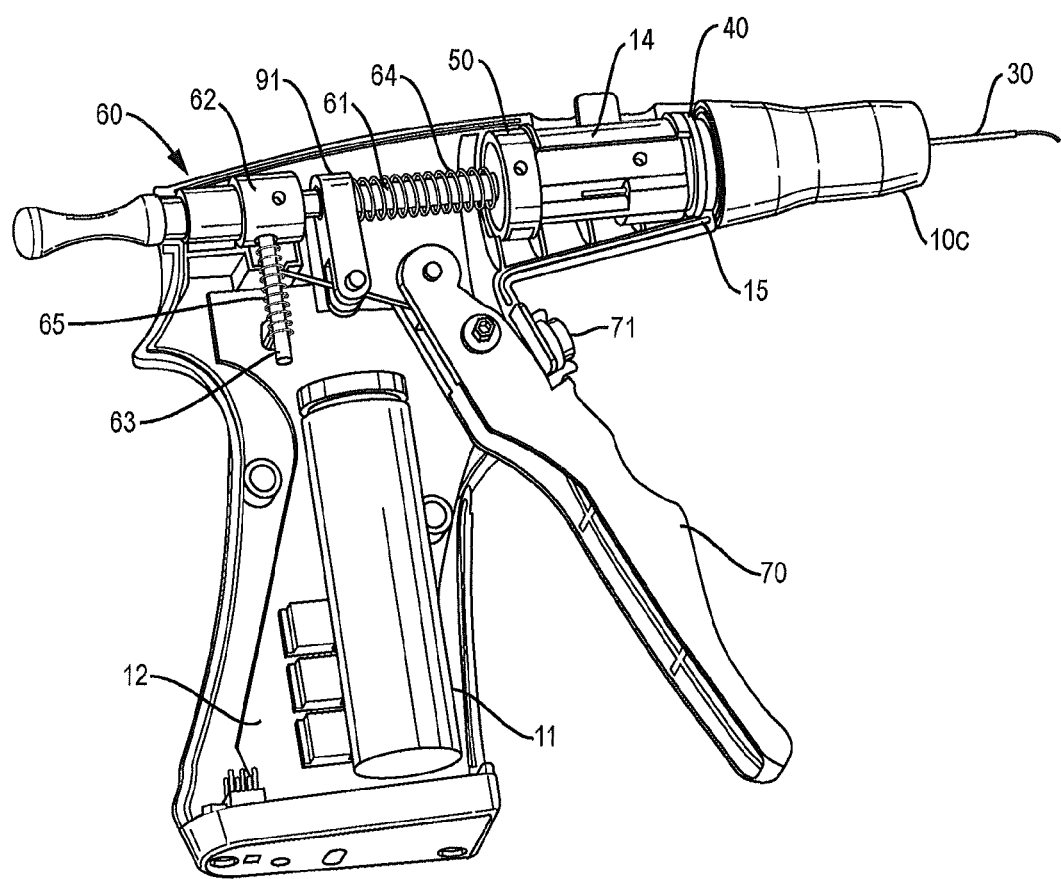
FIG. 2 is a perspective view illustrating an inner view of the dental obturation system according to the embodiment of the present invention shown in FIG. 1.
Figure 3:
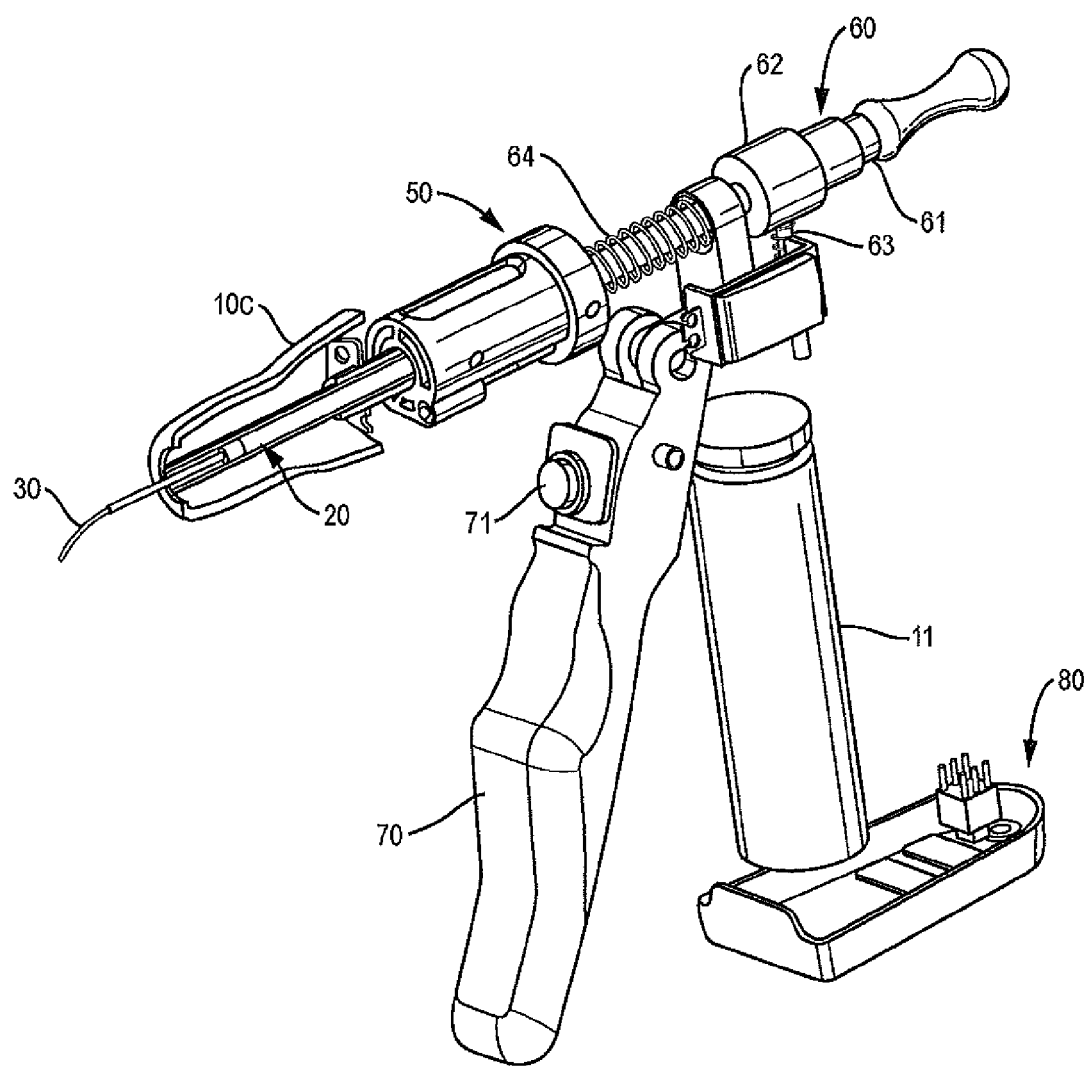
FIG. 3 is an exploded perspective view illustrating interior components of a dental obturation system according to an embodiment of the present invention with the housing from FIG. 1 removed.
Figure 4:
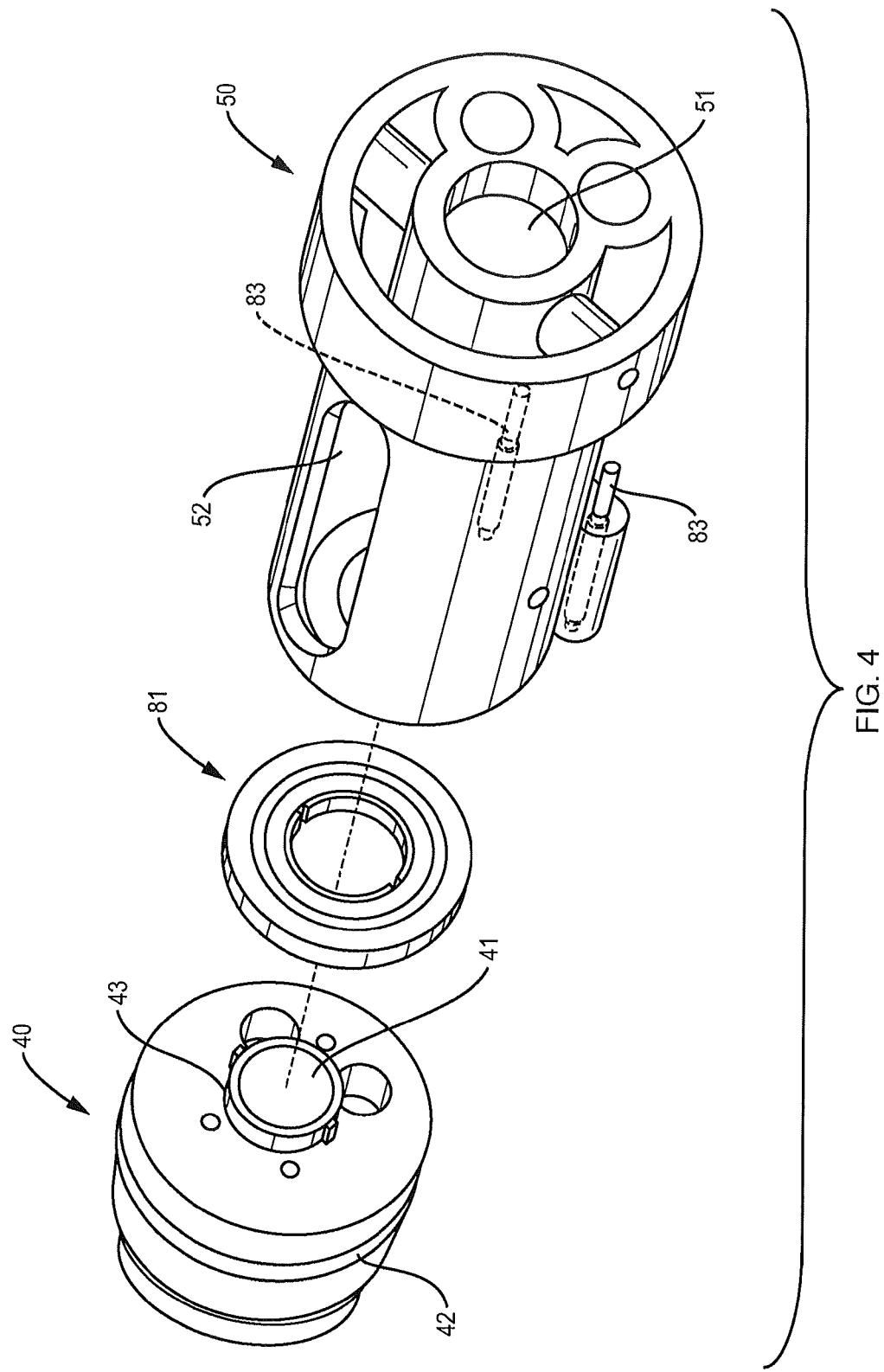
FIG. 4 is an exploded perspective view illustrating a rotary unit, a cartridge unit and a power terminal unit shown in FIGS. 1 through 3.
Figure 5:
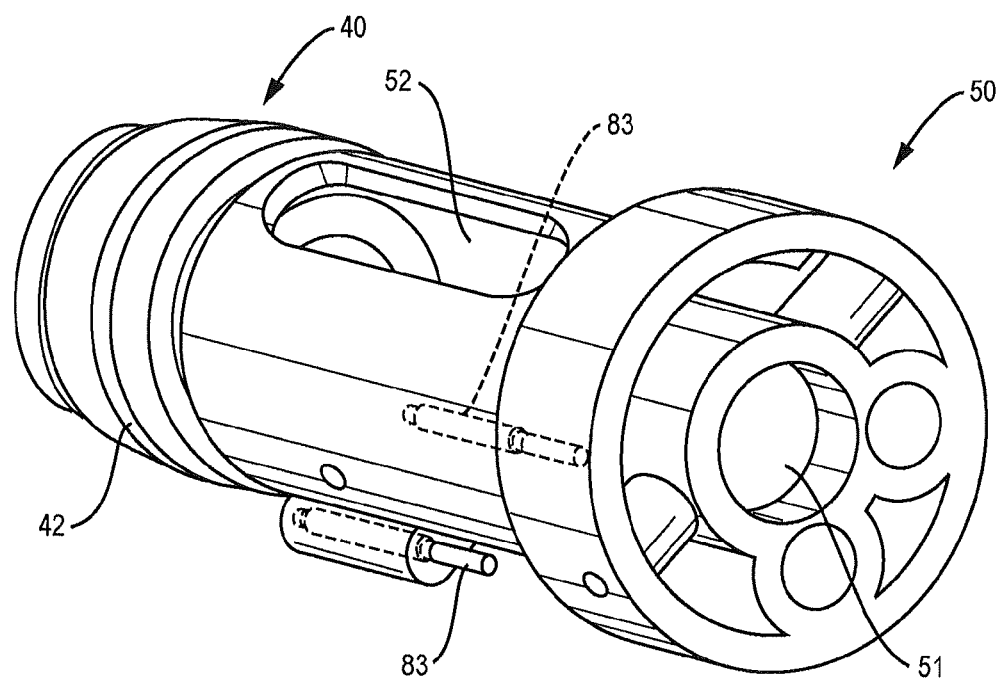
FIG. 5 is an assembled perspective view illustrating a rotary unit, a cartridge unit and a power terminal unit shown in FIGS. 1 through 3.

Hereinbelow, a dental obturation system according to an embodiment of the present invention will be described in detail with reference to the accompanying drawings.

With reference to FIGS. 1 through 5, the dental obturation system according to the embodiment of the present invention includes a gun-shaped main body 10, a heating unit 20 installed in a front end of the main body 10 and heating a filling material, a needle member (micro tube) 30 connected to a front end of the heating unit 20, a rotary unit 40 connected to the heating unit 20 and rotatably installed in the main body 10, a cartridge unit 50 installed in the main body 10 and charged with the filling material therein, a piston unit 60 movably installed in the main body 10 such that the piston unit 60 can be moved forwards and backwards and can feed the filling material charged in the cartridge unit 50 to the needle member 30 under pressure through the heating unit 20, a trigger 70 mounted to the main body 10 and actuating the piston unit 60, and a power terminal unit 80 installed such that it corresponds both to the rotary unit 40 and to the cartridge unit 50 and can supply electric power regardless of an operational state of the rotary unit 40.

The main body 10 includes a grip housing 10a functioning as a grip of the main body and receiving both a battery 11 and a circuit board 12 therein, an upper housing 10b connected to an upper end of the grip housing 10a and receiving the rotary unit 40, the cartridge unit 50 and the piston unit 60 therein, and a front housing 10c connected to a front end of the upper housing 10b and surrounding both the heating unit 20 and a part of the needle member 30.

The trigger 70 is rotatably mounted to the grip housing 10a and the piston unit 60 is actuated in conjunction with a triggering motion of the trigger 70. In other words, when a user holding the trigger 70 with the fingers pulls the trigger toward the grip housing 10a, a piston member 61 of the piston unit 60 can be moved forwards. To realize the above-mentioned operation, the piston member 61 is connected to the trigger 70 using a cooperating unit 91.

Further, the trigger 70 is provided with a switch 71 for controlling the ON/OFF operation of the heating unit 20, and a torsion spring is installed on the rotating center of the trigger 70 and biases the pulled trigger 70 towards the original position thereof. The battery 11 supplies electricity to the heating unit 20.

A charging port 13 is formed in the upper end of the upper housing 10b and allows the filling material to be inserted into the cartridge unit 50 therethrough. A covering member 14 for opening or closing the charging port 13 is provided at a location corresponding to the charging port 13. The covering member 14 is movably installed in a space between the upper housing 10b and the cartridge unit 50, thus preventing foreign substances, such as dust, from infiltrating into the cartridge unit 50.

The front housing 10c is mounted to the front end of the upper housing 10b. A protective cover (heater cover) 16 may be installed in the front housing 10c. The protective cover 16 surrounds and covers the heating unit 20, thus protecting patients and operators from heat generated from the heating unit 20. Described in detail, the protective cover 16 is made of a silicone material. Because the protective cover 16 is a member, which comes into contact with the mouth of the patient, the protective cover 16 is configured to be subjected to wet heat pasteurization (autoclave) at high temperatures of 130° C.~150° C. and is installed such that it can be efficiently isolated from the heat of a heater.

Further, to intercept radiant heat emitted from the heating unit 20, a Teflon® (i.e. polytetrafluoroethylene) pipe 17 (see FIG. 6) may be installed between a heating member (heater) 21a and the protective cover 16.

Figure 6:
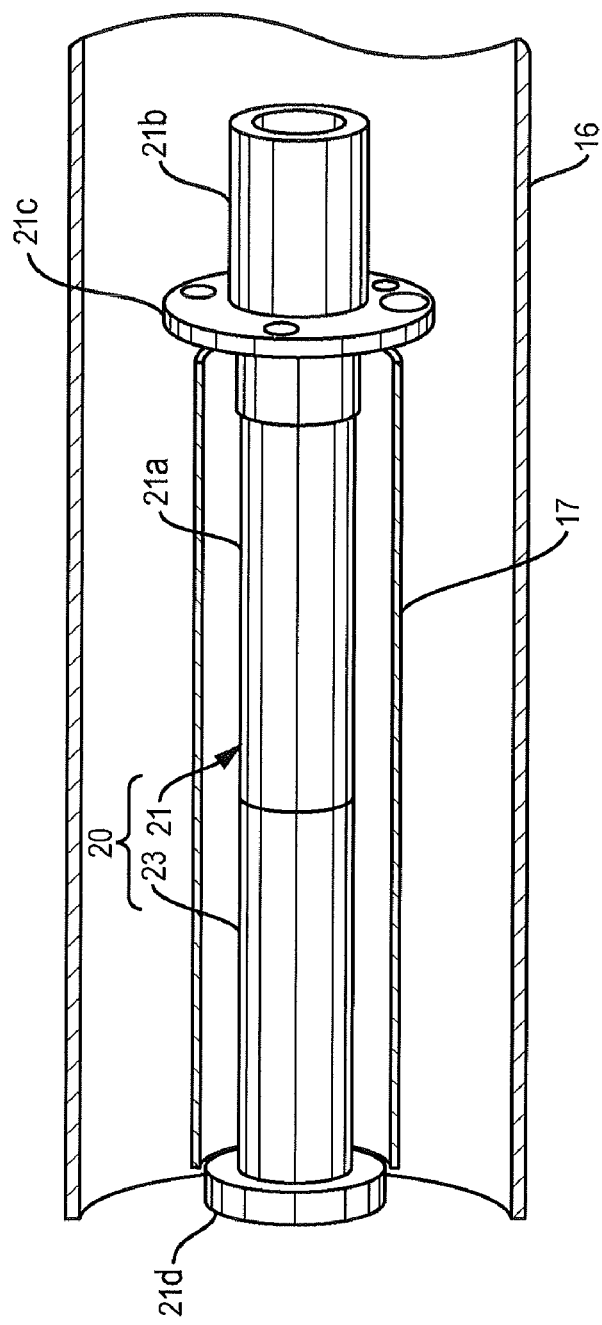
FIG. 6 is a perspective view illustrating a heating unit shown in FIG. 1.

As shown in FIG. 6, the heating unit 20 includes a cylinder unit 21, at a first end of which the needle member 30 is mounted, and a heater 23 surrounding the cylinder unit 21. The second end of the cylinder unit 21 is connected to the rotary unit 40, so that the cylinder unit 21 can be rotated by the rotary unit 40. The cylinder unit 21 includes the heating member 21a, which is surrounded by the heater 23, an insert member 21b, which is provided in the second end of the heating member 21a and is connected to the cartridge unit 50 after passing through the rotary unit 40, and a locking flange 21c installed between the heating member 21a and the insert member 21b and mounted to the rotary unit 40. The locking flange 21c is provided with a plurality of screw holes, through which the locking flange 21c can be fastened to the rotary unit 40 using locking screws. Further, the front end of the cylinder unit 21 is provided with a needle mounting member 21d, to which the needle member 30 is mounted.

The heater 23 may use a heating wire, which is installed to surround the heating member 21a of the cylinder unit 21, or may use one of a variety of heaters having different types and shapes. The heater 23 is electrically connected to the power terminal unit 80 and can be operated in response to electricity supplied from the battery 11 according to operation of the switch 71, and can heat the cylinder unit 21.

The needle member 30 may be mounted to the front end of the cylinder unit 21 using locking screws such that the needle member 30 can be changed with a new one when necessary. The needle member 30 has a micro tube shape, which gradually narrows as it goes towards the tip, so that the needle member 300 can obturate a desired place with the filling material when dental treatment is being administered. Further, the shape of the tip of the needle member 30 may be a bent or straight shape.

The rotary unit 40 is combined with the cylinder unit 21 such that the cylinder unit 21 can be rotated along with the rotary unit 40. The rotary unit 40 is rotatably installed in the upper housing 10b and has a cylindrical shape having a bore 41. In other words, the rotary unit 40 is mounted to the cylinder unit 21 using locking members, such as the locking screws, with an annular groove 42 formed around the outer circumferential surface of the rotary unit 40. A guide rib 15 is formed in the upper housing 10b at a location corresponding to the annular groove 42. Therefore, the rotary unit 40 can be stably rotated without being moved forwards or backwards thanks to engagement of the annular groove 42 with the guide rib 15.

Figure 7:
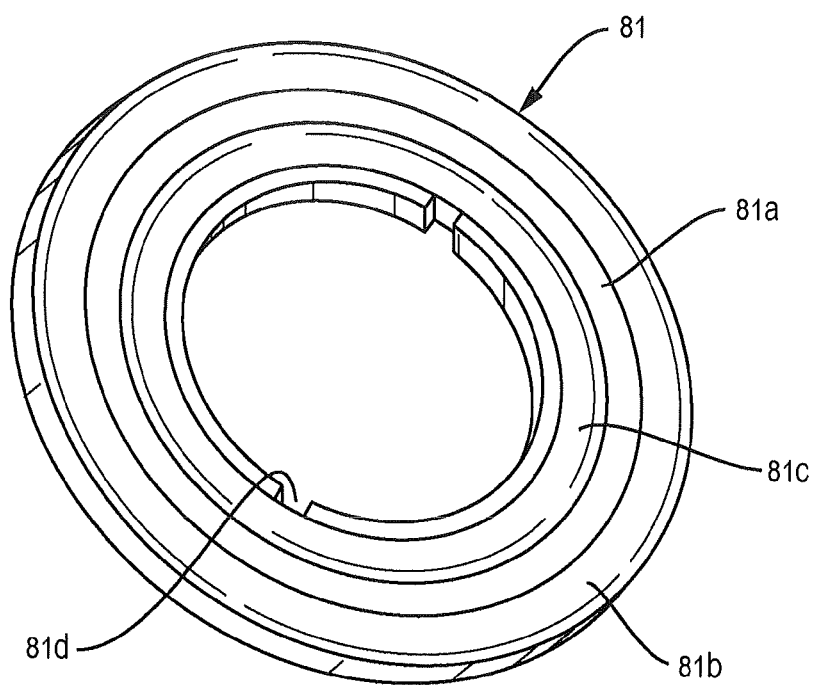
FIG. 7 is a perspective view illustrating a first terminal member shown in FIG. 4.
Figure 8:
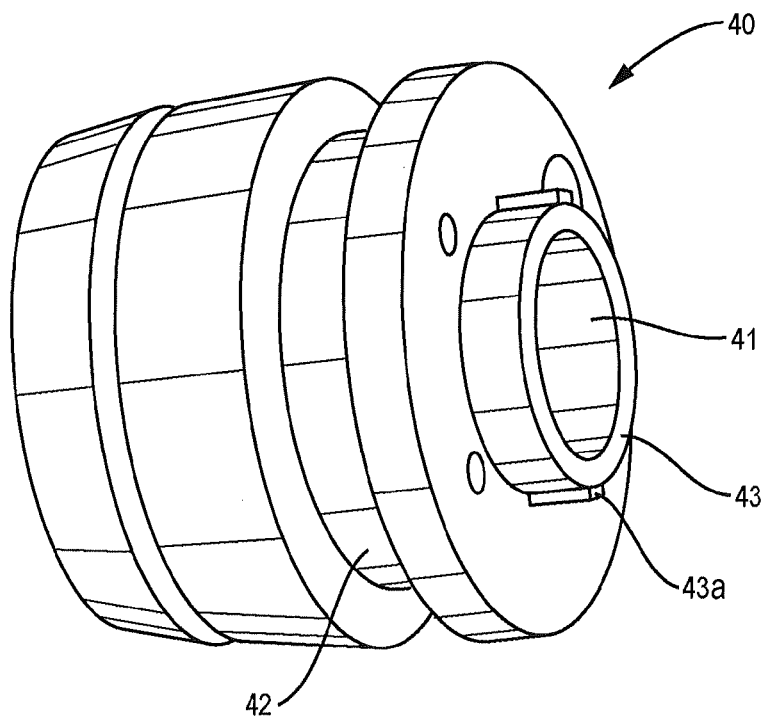
FIG. 8 is an angled forward facing perspective view illustrating a side of the rotary unit shown in FIG. 4 looking away from the piston unit.
Figure 9:
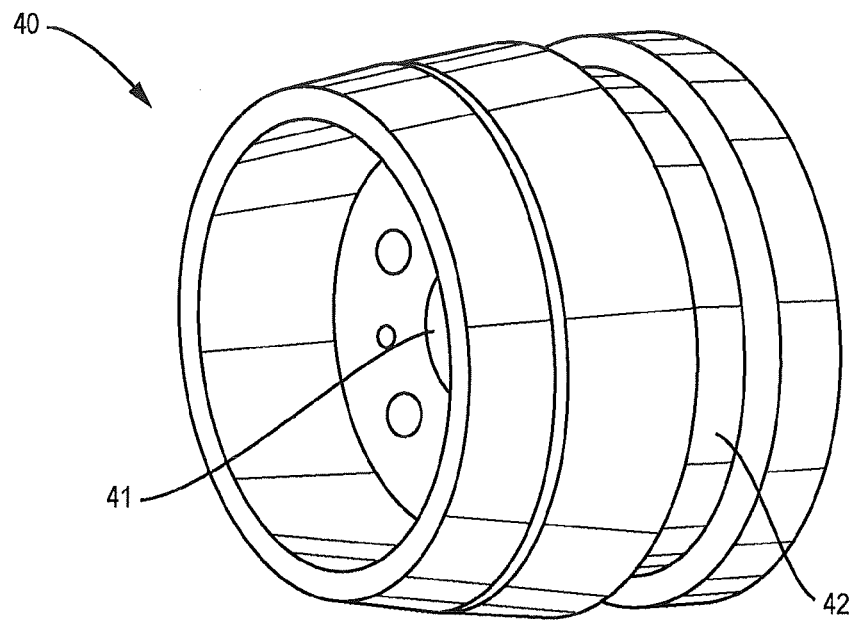
FIG. 9 is an angled rearward facing perspective view illustrating a side of the rotary unit shown in FIG. 4 looking toward the piston unit.
Figure 10:
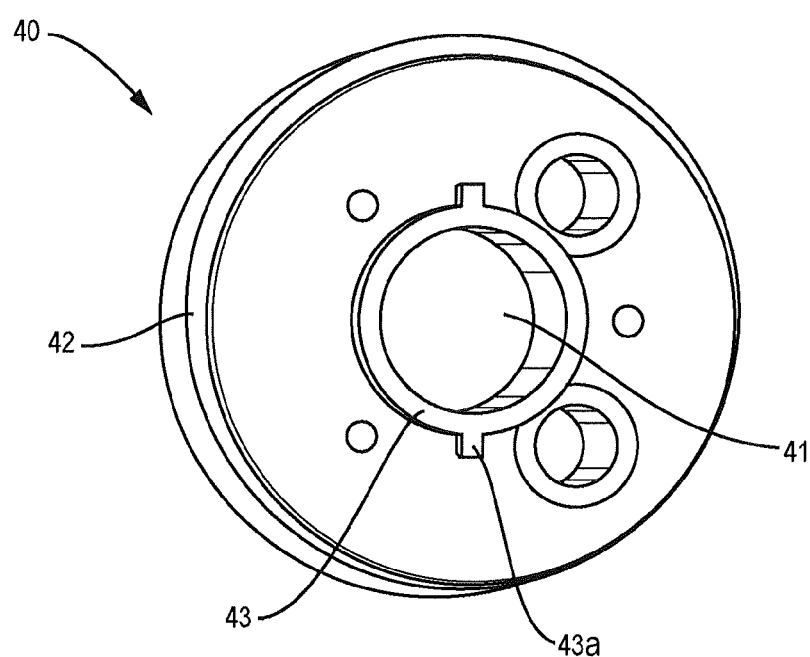
FIG. 10 is a frontal perspective view illustrating the rotary unit shown in FIG. 4 looking away from the piston unit.

Further, as shown in FIGS. 8 through 10, the rotary unit 40 is provided with a bushing part 43 on an end surface thereof, on which the rotary unit 40 faces the cartridge unit 50, and a first terminal member 81 is fitted over the bushing part 43 as will be described later herein. As shown in FIG. 7, the bushing part 43 is provided with a locking rib 43a at a location around the outer circumferential surface thereof. The locking rib 43a engages with a locking notch 81d, which is formed in the edge of an opening of the first terminal member 81. The protective cover 16 is fitted over the rear end of the rotary unit 40.

Figure 11:
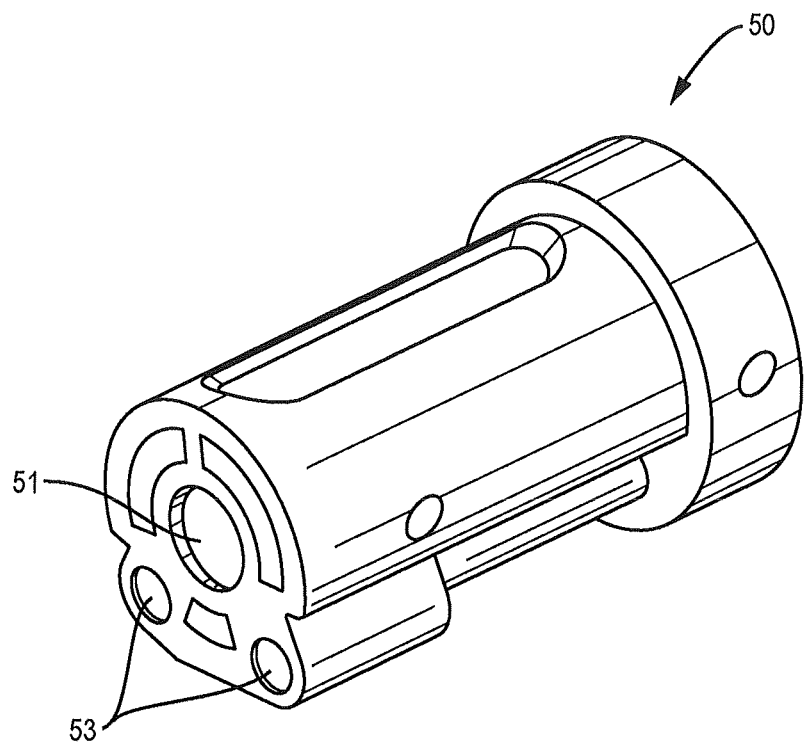
FIG. 11 is an angled rearward facing perspective view illustrating a side of the cartridge unit shown in FIG. 4 looking toward the piston unit.
Figure 12:
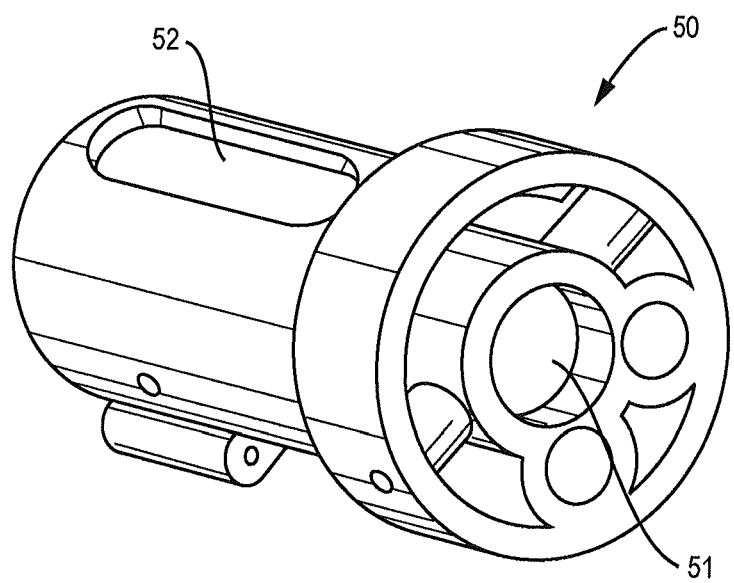
FIG. 12 is an angled forward facing perspective view illustrating a side of the cartridge unit shown in FIG. 4 looking away from the piston unit.

With reference to FIGS. 11 and 12, the cartridge unit 50 is installed in the upper housing 10b such that the cartridge unit 50 is not movable in the upper housing 10b. The cartridge unit 50 has a bore 51, through which the piston unit 60 passes, with an inlet opening 52 formed in the outer circumferential wall of the cartridge unit 50 such that the filling material can be charged in the bore 51 through both the charging port 13 and the inlet opening 52. The filling material, which was charged in the cartridge unit 50 through the inlet opening 52, can be compressed by a reciprocating motion of the piston unit 60 and can be fed to both the heating unit 20 and the needle member 30. Further, the lower part of the cartridge unit 50 is provided with a pair of terminal support holes 53 for supporting respective second terminal members 83 as will be described later herein.

The piston unit 60 includes the piston member 61, which passes through the heating unit 20, the rotary unit 30 and the cartridge unit 40, a piston support 62 installed in the upper housing 10b and supporting the piston member 61, and an anti-reverse rod 63, which is biased by a spring 65 and prevents free backward movement of the piston member 61.

In the piston unit 60 having the above-mentioned construction, the piston member 61 is coupled to the cooperating unit 91 operating in conjunction with the trigger 70. Therefore, the piston member 61 coupled to the cooperating unit 91 can move forwards in response to a triggering motion of the trigger 70 and can feed the filling material charged in the cartridge unit 50 to the heating unit 20. When an external force is removed from the trigger 70, the advanced piston member 61 can return to the original position thereof by the restoring force of a spring 64. The anti-reverse rod 63 is inserted into the piston support 62 and is biased toward the piston member 61 by the spring 65, thus providing a frictional force to the piston member 61 and preventing the piston member 61 from naturally moving backwards.

The power terminal unit 80 realizes an electric connection between the rotary unit 40 and the cartridge unit 50, and includes the first terminal member 81 combined with the rotary unit 40 and the second terminal members 83 installed in the cartridge unit 50 such that the second terminal members 83 can be electrically connected to the first terminal member 81.

Here, as shown in FIGS. 4 through 7, the first terminal member 81 includes an annular substrate 81a, with first and second terminals 81b and 81c formed on the substrate 81a. The first and second terminals 81b and 81c individually have an annular shape and are separated from each other. The substrate 81a is combined with the rotary unit 40 in a state in which the substrate 81a is in close contact with the rotary unit 40. In the above state, the substrate 81a has a central opening and is fitted over the bushing part 43 of the rotary unit 40 by the opening. Further, to make the substrate 81a rotate along with the rotary unit 40 without being rotated relative to the rotary unit 40 in a state in which the substrate 81a is combined with the rotary unit 40, the locking notch 81d is formed in the edge of the opening of the substrate 81a and realizes an engagement of the substrate 81a with the rotary unit 40.

Each of the first and second terminals 81b and 81c preferably protrudes from a surface of the substrate 81a and, more preferably, protrudes from the surface of the substrate 81a so as to have a semi-circular cross-section. Further, the first and second terminals 81b and 81c are concentrically formed on the substrate 81a so that the terminals 81b and 81c form respective annular shapes with a different radius. The first and second terminals 81b and 81c form a positive electrode and a negative electrode, respectively, and are electrically distanced apart from each other. Further, the first and second terminals 81b and 81c are electrically connected to the heater 23 by respective electric wires (not shown) in a state in which the first and second terminals 81b and 81c are supported on the substrate 81a.

Further, a pressure member is preferably provided between the first terminal member 81 and the rotary unit 40 such that the electric contact between the first terminal member 81 and the second terminal members 83 can be stably maintained.

The second terminal members 83 each having a terminal pin shape are securely held in the cartridge unit 50 such that they can be electrically connected to the first and second terminals 81b and 81c of the first terminal member 81. The two second terminal members 83 are locked to the respective terminal support holes 53 formed in the lower part of the cartridge unit 50. Further, the two second terminal members 83 are connected to the battery 11 by respective electric wires (not shown) that go through the switch 71.

Due to the above-mentioned construction, the two second terminal members 83 can continuously remain in the state in which the second terminal members 83 are electrically connected to the first and second terminals 81b and 81c of the first terminal member 81, respectively, and can be rotated along with the rotary unit 40 while being securely held in the cartridge unit 50.

Due to the above-mentioned construction, the heating unit connected to the rotary unit 40 can stably receive electricity from the battery 11 through the power terminal unit in a state in which the heating unit 20 and the needle member 30 are installed such that they can both rotate together.

Therefore, when dental treatment is administered using a bent needle member 30 connected to the heating unit 20, an operator can easily manipulate the needle member 30 while rotating both the rotary unit 40 and the heating unit 30 and thereby changing the orientation of the needle member 30 while maintaining his/her posture without changing it. That is, the heating unit 20 can continuously heat the filling material while it is rotating, so that the operator can easily and conveniently obturate a root canal of a patient with the filling material regardless of the location of a decayed tooth of the patient.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A dental obturation system, comprising:
    a main body including a grip housing receiving a battery therein and an upper housing mounted to an upper end of the grip housing;
    a needle member mounted to a front end of the upper housing and configured to fill a place requiring a dental treatment with a heated filling material;
    a heating unit connected to the needle member and configured to heat the filling material to be fed to the needle member;
    a rotary unit installed in the upper housing wherein the rotary unit is combined with the heating unit and rotates along with the heating unit;
    a cartridge unit configured to receive therein the filling material supplied from outside, the cartridge unit being installed in the upper housing so that the cartridge unit faces the rotary unit;
    a piston unit movably installed in the upper housing and configured to feed the filling material from the cartridge unit under pressure in a direction toward both the heating unit and the needle member;
    a trigger rotatably mounted to the main body and configured to actuate the piston unit, thus feeding the filling material; and
    a power terminal unit installed both in the rotary unit and in the cartridge unit and configured to maintain an electric connection between the rotary unit and the cartridge unit so that the power terminal unit can apply electricity of from the battery to the heating unit even when the rotary unit is rotating,
    wherein the cartridge unit is installed in the upper housing so that the cartridge unit faces the rotary unit, and the cartridge unit includes a bore configured to allow the piston unit to move therethrough, an inlet opening formed in an outer circumferential wall of the cartridge unit to allow the filling material to be fed into the bore of the cartridge unit, and a pair of terminal support holes configured to support the power terminal unit.

2. The dental obturation system as claimed in claim 1, wherein the rotary unit comprises:
    a bore for allowing the piston unit to be moved therethrough; an annular groove formed around an outer circumferential surface of the rotary unit; and a bushing part protruding from an end of the rotary unit facing the cartridge unit and holding the power terminal unit, with a guide rib provided in the upper housing for engaging with the annular groove and thereby guiding a rotation of the rotary unit while preventing forward or backward movement of the rotary unit.

3. The dental obturation system as claimed in claim 1, wherein the power terminal unit comprises:
    a first terminal member mounted to the rotary unit and electrically connected to the heating unit; and
    a pair of second terminal members installed in the respective terminal support holes of the cartridge unit and configured to maintain a state in which the pair of second terminal members are electrically connected to the first terminal member.

4. The dental obturation system as claimed in claim 3, wherein the first terminal member comprises:
an annular substrate fitted over a bushing part of the rotary unit through an opening and having a locking notch, which is formed in an edge of the opening and is engaged with a locking rib formed around an outer circumferential surface of the bushing part; and
first and second annular terminals concentrically protruding from a surface of the annular substrate and having different radii, wherein
the pair of second terminal members come into contact with the first and second annular terminals, respectively.

5. The dental obturation system as claimed in claim 4, wherein each of the first and second annular terminals protrudes from the surface of the substrate so that each of the first and second terminals has a semi-circular cross-section.

6. The dental obturation system as claimed in any one of claims 2 through 5, wherein
the upper housing is provided with a charging port for charging the cartridge unit with the filling material, wherein the dental obturation system further comprises a covering member movably installed in a space between the upper housing and the cartridge unit such that the covering member can open or close the charging port.

7. The dental obturation system as claimed in any one of claims 2 through 5, wherein the piston unit comprises:
a piston member installed in the upper housing such that the piston member can be moved through the cartridge unit, the rotary unit and the heating unit;
a piston support installed in the upper housing and guiding movement of the piston member; and
an anti-reverse rod combined with the piston member and mounted to the upper housing such that the anti-reverse rod can restrict reverse movement of the piston member.

8. The dental obturation system as claimed in any one of claims 2 through 5, further comprising:
a protective cover made of a silicone material and installed around the heating unit so as to cover the heating unit.

9. The dental obturation system as claimed in claim 8, further comprising:
a polytetrafluoroethylene pipe installed between the heating unit and the protective cover and configured to intercept radiant heat emitted from the heating unit.

* * * * *